United States Patent
Engel et al.

(10) Patent No.: US 7,122,820 B2
(45) Date of Patent: Oct. 17, 2006

(54) METHOD FOR DETERMINING VISIBILITY, AMOUNT OF PRECIPITATION AND TYPE OF PRECIPITATION

(75) Inventors: Stefan Engel, Hamburg (DE); Klaus Heyn, Hamburg (DE)

(73) Assignee: Vaisala Impulsphysik GmbH, Schenefeld (DE)

( * ) Notice: Subject to any disclaimer, the term of this patent is extended or adjusted under 35 U.S.C. 154(b) by 0 days.

(21) Appl. No.: 10/132,748

(22) Filed: Apr. 24, 2002

(65) Prior Publication Data

US 2002/0158215 A1    Oct. 31, 2002

(30) Foreign Application Priority Data

Apr. 25, 2001    (DE)  ................... 101 20 747

(51) Int. Cl.
*G01N 21/49*    (2006.01)
*G01N 21/00*    (2006.01)

(52) U.S. Cl. .................... 250/574; 356/339
(58) Field of Classification Search ........... 250/573, 250/574; 356/337–343
See application file for complete search history.

(56) References Cited

U.S. PATENT DOCUMENTS

| | | | |
|---|---|---|---|
| 3,745,350 A | 7/1973 | Hill et al. .............. | 250/565 |
| 4,123,665 A | 10/1978 | Früngel .................. | 250/565 |
| 4,613,938 A | 9/1986 | Hansen et al. ............. | 702/3 |
| 4,693,602 A | 9/1987 | Wyatt et al. .............. | 356/336 |
| 5,373,367 A | 12/1994 | DeGunther et al. ......... | 356/438 |
| 5,444,530 A | 8/1995 | Wang ...................... | 356/338 |
| 5,604,590 A | 2/1997 | Cooper et al. ............. | 356/338 |

FOREIGN PATENT DOCUMENTS

| | | |
|---|---|---|
| DE | 21 21 088 | 12/1971 |
| DE | 29 16 388 | 11/1979 |
| EP | 0745839 A1 * | 12/1996 |

OTHER PUBLICATIONS

*English Abstract of DE 29 16 388.
Frank W. Gibson "In situ photometric observations of angular scattering from atospheric aerosols" Applied Optics, Oct. 1988, vol. 15, No. 10, pp. 2520-2533.
Ulrich Tietze, et al. "Halbleiter -Schaltungstechnik" Springer Verlag, 11. Auflage 1999, pp. 1215-1219.

* cited by examiner

*Primary Examiner*—Thanh X. Luu
(74) *Attorney, Agent, or Firm*—Reed Smith LLP

(57) ABSTRACT

The invention is directed to a method and a combined visibility measuring and precipitation measuring instrument for determining visibility, amount of precipitation and type of precipitation.

19 Claims, 8 Drawing Sheets

METHOD FOR DETERMINING VISIBILITY, AMOUNT OF PRECIPITATION AND TYPE OF PRECIPITATION

CROSS-REFERENCE TO RELATED APPLICATIONS

This application claims priority of German Application No. 101 20 747.6, filed Apr. 25, 2001, the complete disclosure of which is hereby incorporated by reference.

BACKGROUND OF THE INVENTION a) Field of the Invention

The invention is directed to a method for determining visibility, amount of precipitation and type of precipitation, and to a combined visibility and precipitation measuring instrument, particularly for distinguishing between different types of precipitation and amounts of precipitation.

b) Factors Relating to the Invention

Measurement of environmental parameters and weather parameters is growing in importance. In order to replace former visual observations with automatic detection of weather phenomena and, accordingly, in order gradually to enable a complete automation of weather stations, the availability of measurement instruments capable of determining as many of the required parameters as possible is required.

Atmospheric turbidity is brought about by aerosols whose type and concentration determine visibility. In this connection, there are two physical effects that are important in determining visibility with optical measuring instruments. Irradiation of a measurement volume by a light source produces light scattering on the one hand and light absorption on the other hand.

Both effects are detected by a transmissometer arrangement because the latter evaluates what percentage of the emitted light reaches the location of the receiver. The reception signal is influenced by scattering at the aerosols as well as by absorption by the aerosols. Both phenomena are covered under the concept of extinction, wherein the absorption may be disregarded in favor of scattering. Transmissometers measure the atmospheric extinction coefficient directly. The visibility can then be determined by definition by way of the relationship described by Koschmieder.

Apart from the large air volume utilized for determining visibility, the advantage of transmissometers consists in this definite relationship between transmission and visibility. The quality of the measurement performance of transmissometers is generally very highly rated.

Nevertheless, there are reasons in favor of using a simplified measurement concept such as that offered by scattered light measurement devices:

greater visibility measurement range;

possibility of determining the type and intensity of precipitation;

low initial costs;

reduced space requirement; the typical distance of the transmitter and scattered light receiver from the measurement volume is less than 1 m;

no aligning or adjusting labor is required;

reduced influence of contaminated device plates on measuring performance;

simple calibration; and low maintenance costs.

c) Description of the Related Art

In scattered light measurement devices such as those described in DE-OS 21 21 088, a receiver is positioned at an appropriate angle to the light source. The light component scattered by the aerosols and precipitation particles in the measurement volume at this angle is determined. In this case, knowledge of the relationship between the optical scattering function and the atmospheric extinction coefficient is required for evaluating the reception signal.

Differences in the scattering behavior between the various particles cannot be taken into account adequately, or at all, in conventional scattered light measuring instruments by measuring either at a selected scattering angle or over the largest possible scattering angle area.

The conventional devices realize methods that are based on the assumption that the utilized scattering angles in the light wavelength used for the measurement can be taken as representative for all occurring phenomena.

In this connection, a forward scattering angle of approximately 30° to 40° has proven to be representative for a large number of types, mixtures and concentrations of aerosols based on various simulations of atmospheric models and practical tests and comparisons for the visible wavelength range. In general, the theory of scattering proposed by Mie applies for this order of magnitude of particles with much greater diameters than the light wavelength. However, different assessments of the measured scattering signal are also necessary in this case because there are significant differences in the scattering behavior of mist and fog.

There are very many greater influences when considering precipitation. Drizzle droplets and raindrops, hail, soft hail or snow pellets, and snowflakes result in entirely different scattering behavior for which it is no longer possible to carry out the same evaluations of the measured scattering signal as those for mist and fog. Further, these particles do not remain in a quasi-stationary spatial position; rather, because of their size, they undergo a movement in the direction of the ground so that the period during which they remain in the measurement volume is limited.

OBJECT AND SUMMARY OF THE INVENTION

It is the primary object of the invention to provide a method and an arrangement which ensure the ability to distinguish easily between different phenomena such as fog, rain, snow, and so on.

According to the invention, this object is met in an instrument for measuring visibility and precipitation containing a light transmitter, at least one receiver in forward scattering arrangement and evaluating electronics in that a first receiver is arranged opposite to the light transmitter, a second receiver is arranged in a forward scattering angle range of 20° to 40°, a third receiver is arranged in a forward scattering angle range of 70° to 120°, and a fourth receiver is arranged in a forward scattering angle range of 140° to 150°, a modulation generator is arranged in front of the light transmitter, and every receiver communicates with the evaluating electronics via a postamplifier and a synchronous rectifier.

Advisable constructions are characterized by the subclaims.

The invention will be described more fully in the following with reference to embodiment examples shown in the accompanying drawings.

DESCRIPTION OF THE PREFERRED EMBODIMENTS

Figure 1:
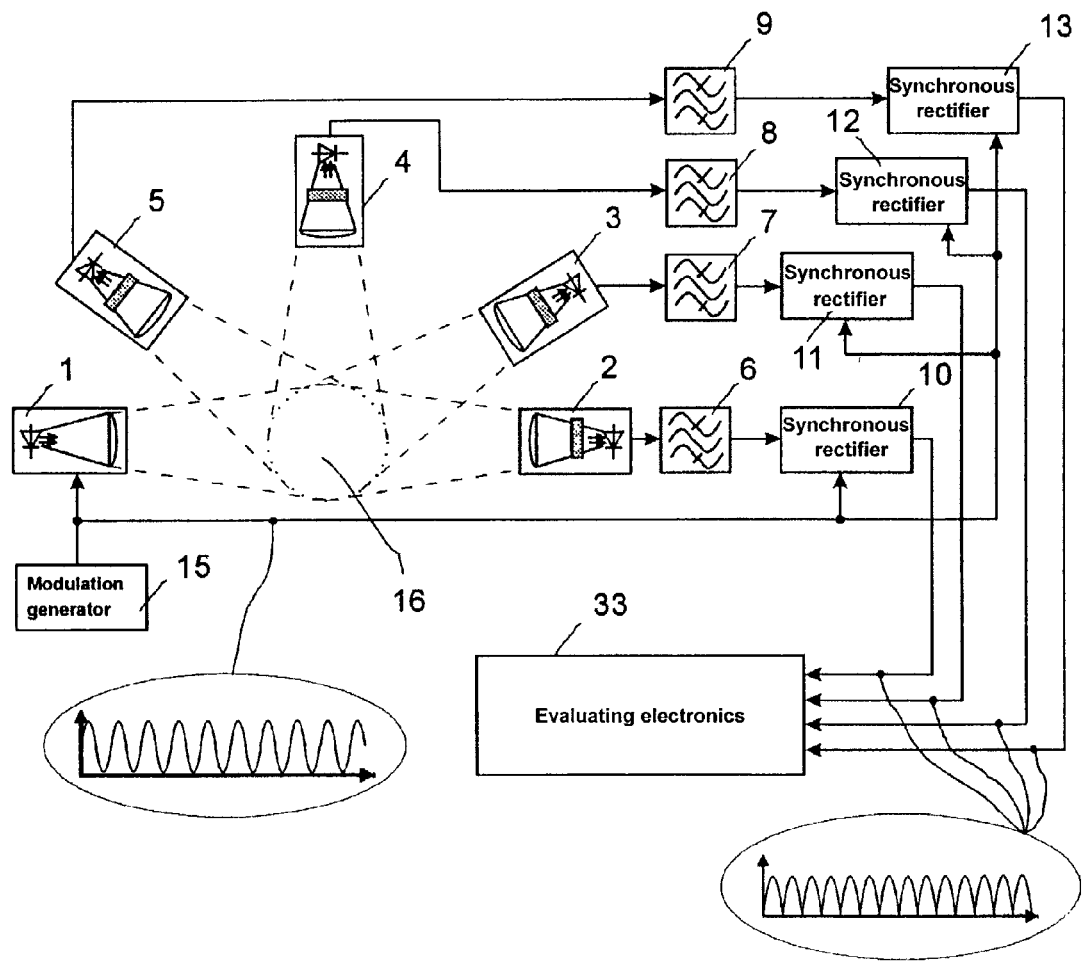
FIG. 1 shows a schematic construction of an instrument according to the invention.
Figure 3:
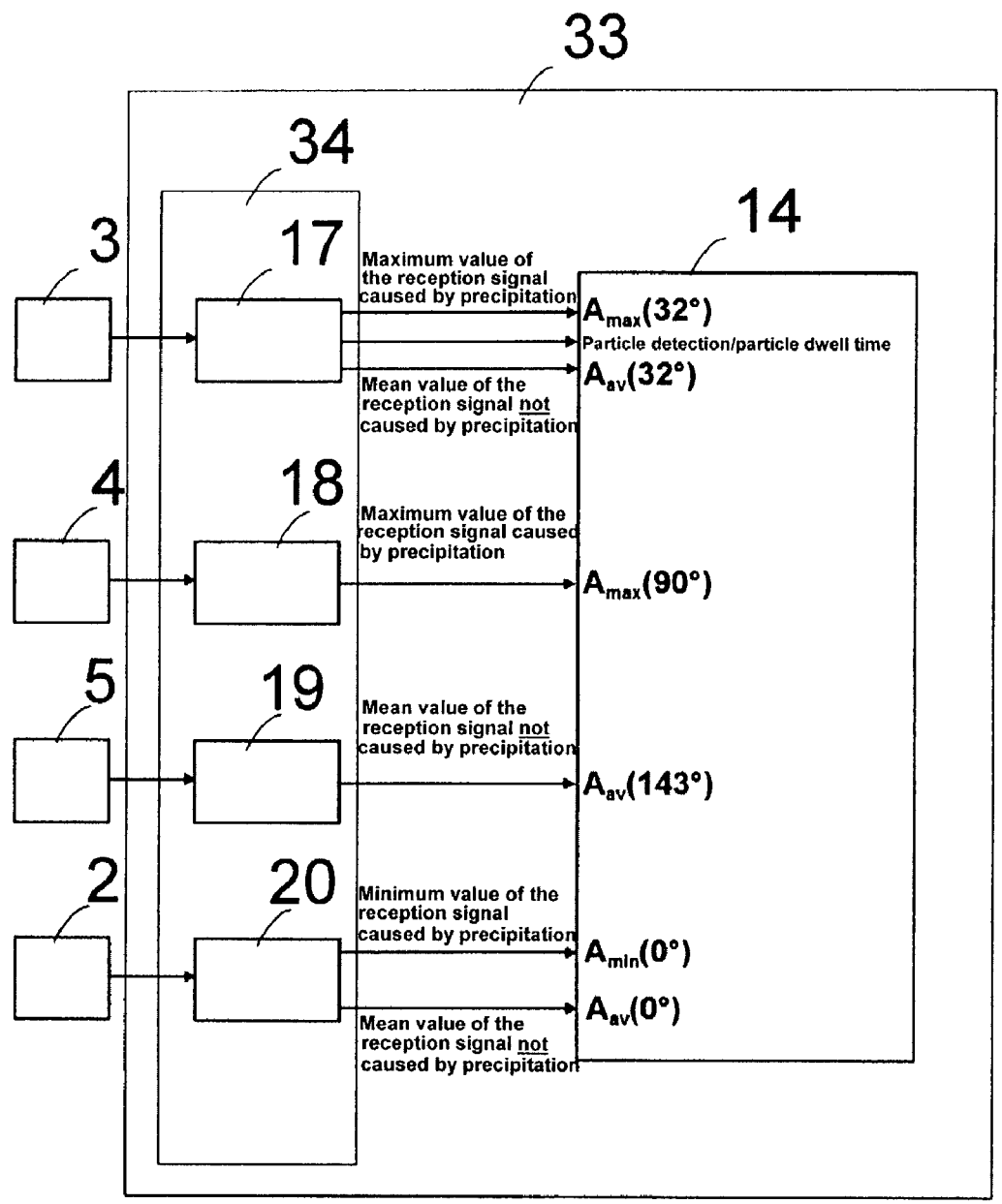
FIG. 3 shows a block diagram of the evaluating electronics.

FIG. 1 shows the essential components of the arrangement according to the invention, comprising the light transmitter 1, the four optoelectronic receivers 2, 3, 4, 5, each of which is connected to the common processing unit 14 (as shown in FIG. 3) via a postamplifier 6, 7, 8, 9 and subsequent synchronous rectifiers 10, 11, 12, 13, and the modulation generator 15. The optoelectronic receiver 2 is located opposite to the light transmitter 1 and the other optoelectronic receivers 3, 4 and 5 are arranged at measurement angles of 32°, 90° and 143°, respectively. The measurement volume 16, as it is called, is formed in the intersection area of the viewing fields of the optoelectronic receivers 2, 3, 4, 5 and of the light bundle emitted by the light transmitter 1.

The measurement volume 16 is illuminated in a defined manner at least several thousand times per second by the light transmitter 1 with a narrow light cone. The emitted light is intensity-modulated (e.g., sinusoidally) and has a defined wavelength.

For reasons relating to independence of the measurement from daylight and to improve the signal-to-noise ratio, the intensity of the light source is modulated by the modulation generator 15 at a frequency greater than 1 kHz. The optoelectronic receivers 2, 3, 4, 5 are provided with optical bandpass filters which are transparent only for the wavelength used by the light transmitter 1. The postamplification of the received signals is carried out in in a narrow band around the modulation frequency. Rectification is carried out in the subsequent synchronous rectifiers 10, 11, 12, 13 in rigid phase ratio to the modulation frequency and the signals are then fed to evaluating electronics 33.

The spatial arrangement of the light transmitter 1 and receivers 2, 3, 4, 5 is selected so as to take into account the opening angles of the transmitter unit and receiver units such that the resulting measurement volume size ensures that only one particle at a time remains in the measurement volume 16 at the anticipated maximum spatial occurrence density of precipitation particles during the heaviest precipitation. Individual particle detection is made possible in this way.

Figure 2:
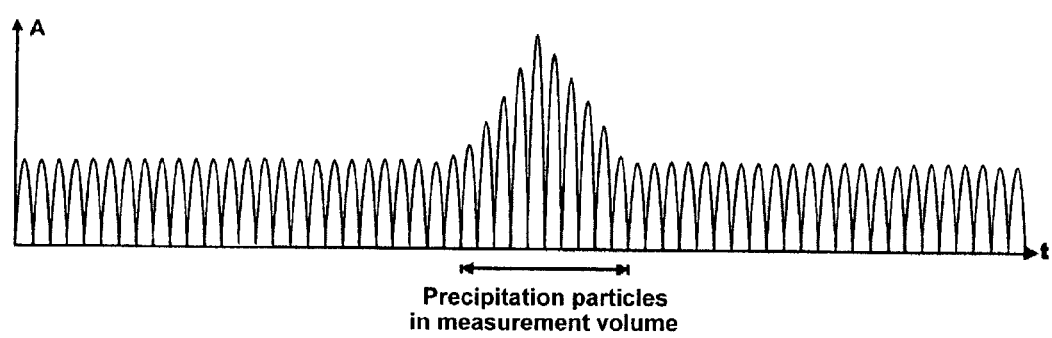
FIG. 2 shows a measurement signal graph.

Since these particles, because of their size, generate a sufficiently large scattering signal which can be distinguished from the aerosols that are otherwise present, it is possible to detect the presence of precipitation particles generally by a time-discrete analysis of the scattering signals. The raw signal shown in FIG. 2 is the reception signal typically obtained by the measuring arrangement when a precipitation particle penetrates the measurement volume 16.

The signal amplitudes produced by a precipitation particle can be definitely distinguished from the signal that is unrelated to precipitation. Therefore, by comparing the spontaneous signal to the mean signal value, it is possible to make conclusive judgments about whether or not a precipitation particle is present in the measurement volume 16.

This information, together with the usual time-continuous reception signal evaluation, also makes possible a time-discrete handling of precipitation particles.

Significant measurement quantities for every detected precipitation particle are the quantity of half-waves per precipitation event and the maximum signal amplitude occurring in this connection.

When these steps for signal handling are carried out in all participating receivers 2, 3, 4, 5, it is possible to directly evaluate absolute values and distinguish between the magnitudes of the scattering signals in a time-averaged manner as well as for every individual precipitation particle event separately, that is, a precipitation particle is detected when it penetrates into the measurement volume 16 and the dwell time in the measurement volume 16 and the signal amplitude occurring because of the particle are recorded.

Based on the individual particle detection described above, the present invention makes it possible to separate the precipitation-related reception signal components from the reception signal components that are not related to precipitation.

The raw signals obtained at different angles by means of the receivers 2, 3, 4, 5 are initially conditioned in the following manner according to FIG. 3 in the evaluating electronics:

1. The following information and measurement quantities are derived from the raw signal obtained by the receivers 3 by means of the first reception signal conditioning 17 (according to FIG. 4) and are made available for further processing:

the presence of a precipitation particle in the measurement volume 16 is registered, the maximum value of the reception signal is determined for every individual precipitation particle penetrating the measurement volume 16 →>$A_{max}(32°)$, the mean value of the scattering signal is determined, wherein the influence of precipitation particles on this mean value is prevented →>$A_{av}(32°)$.

2. By means of the second reception signal conditioning 18 (according to FIG. 5), the maximum value of the reception signal for every individual precipitation particle detected at 32° is determined from the raw signal obtained by the receiver 4 →>$A_{max}(90°)$.

3. By means of the third reception signal conditioning 19 (according to FIG. 6), the mean value of the scattering signal is formed from the raw signal obtained by receiver 5, wherein the influence of precipitation particles on this mean value is prevented →>$A_{av}(143°)$.

Figure 7:
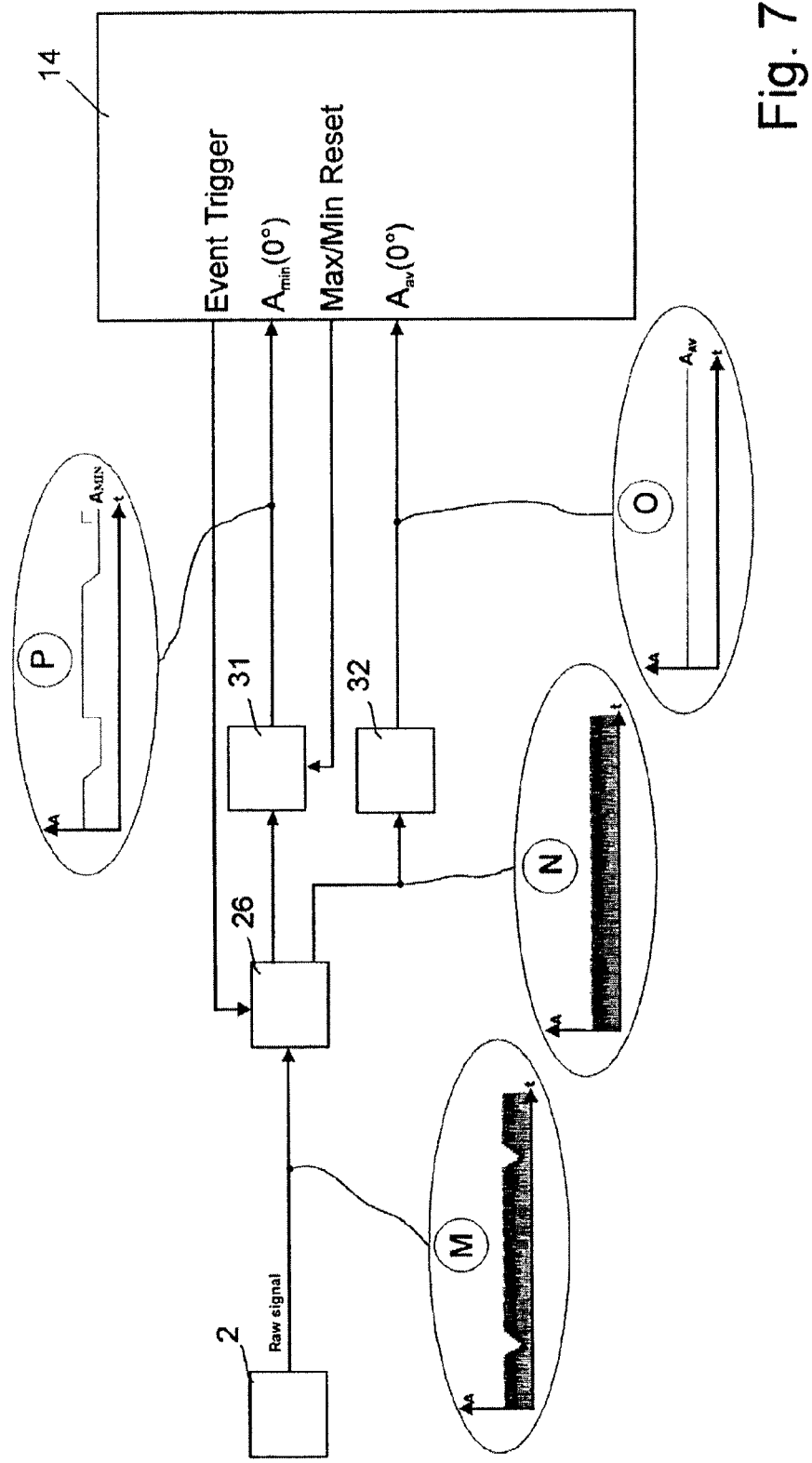
FIG. 7 is a schematic view illustrating the fourth reception signal conditioning.

4. The following measurement quantities are derived from the raw signal obtained by the receiver 2 by means of the fourth reception signal conditioning 20 (according to FIG. 7):

minimal value of the reception signal for every individual precipitation particle penetrating the measurement volume 16 →>$A_{min}(0°)$;

mean value of the reception signal, wherein the influence of precipitation particles on this mean value is likewise prevented →>$A_{av}(0°)$;

The corresponding signals are obtained in the manner described in detail in the following with reference to FIGS. 4 to 7.

Figure 4:
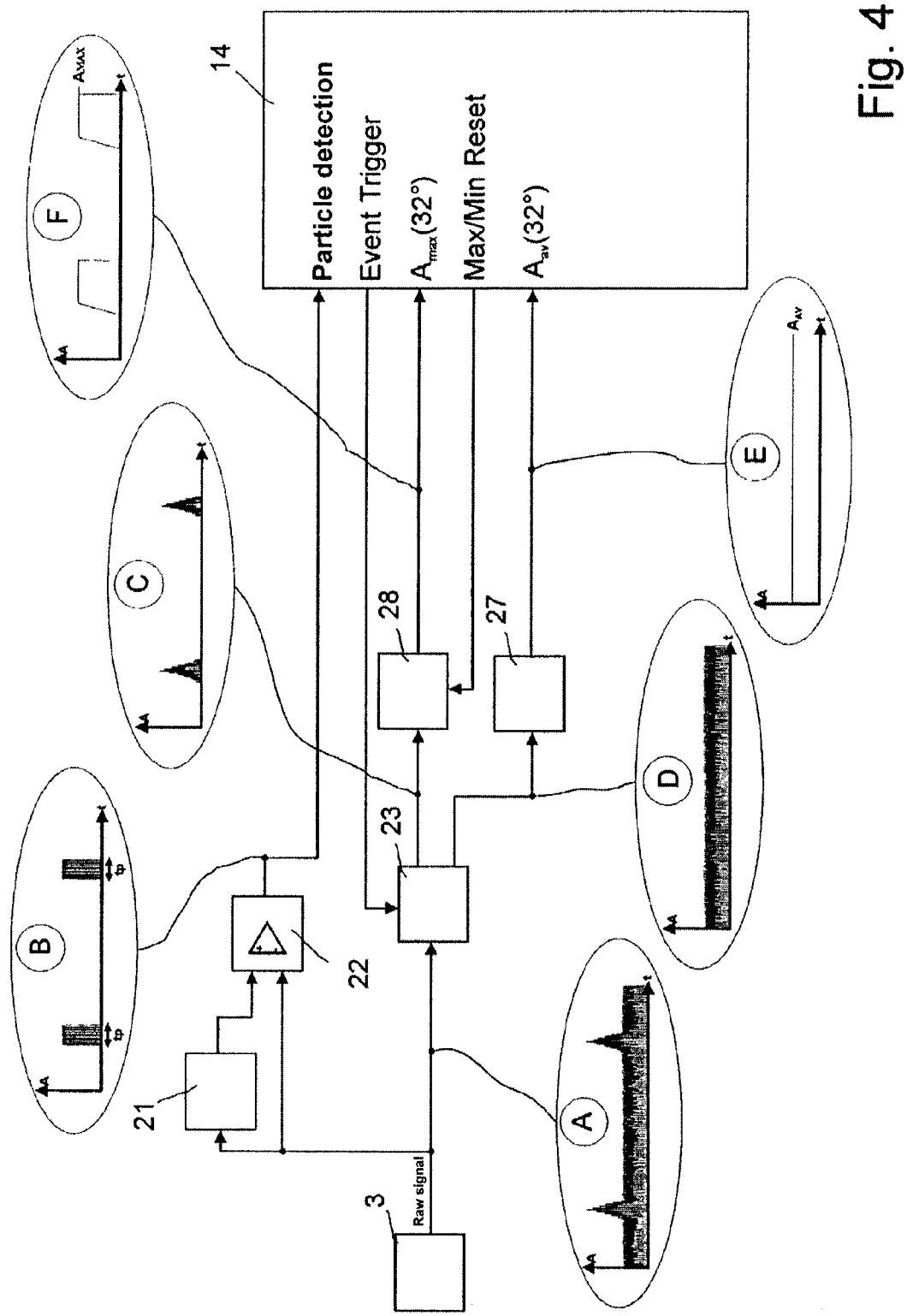
FIG. 4 is a schematic view illustrating the first reception signal conditioning.

According to FIG. 4, the raw signal A obtained by the receiver 3 at 32° is supplied for averaging to the lowpass 21 and, in parallel, to the first input of the threshold switch 22.

The output of the lowpass 21 is linked to the second input of the threshold switch 22. Due to the fact that a precipitation particle causes a reception signal that is greater than the mean signal value, it can be decided on the basis of a comparison between the mean reception signal value and the spontaneous signal (reception signal that is not averaged) whether or not a precipitation particle is actually located in the measurement volume 16. The threshold switch 22 is used for this purpose. When a precipitation particle penetrates into the measurement volume 16, a rectangular pulse is generated at the output of the threshold switch 22 for every modulation signal half-wave as long as the precipitation signal remains in the measurement volume 16 (signal sequence B). On the one hand, this rectangular pulse sequence is used in the processing unit 14 for determining the particle dwell time. On the other hand, the "event trigger" signal which serves as a control signal for the signal separating units 23, 24, 25 and 26 is derived therefrom. The event trigger signal indicates whether or not a precipitation particle is actually located in the measurement volume.

With the assistance of the event trigger signal, the signal separating unit 23 is capable of freeing the raw signal A obtained at 32° from precipitation-related components and delivers signal sequence D via its first output. This reception signal component which is not related to precipitation is subsequently averaged and, for this reason, is supplied via the lowpass 27. Signal sequence E is formed. The precipitation-related signal component is generated at the second output of the signal separating unit 23 and is fed to the maximum value detector 28. In this way, the maximum value of the signal amplitude caused by the precipitation particle is made available to the processing unit 14 (signal sequence F). After the precipitation particle has exited from the measurement volume 16, this measured value is read out from the processing unit 14 and the maximum value detector 28 is reset by means of the control signal Max/Min Reset and is thus prepared for the next measurement.

Figure 5:
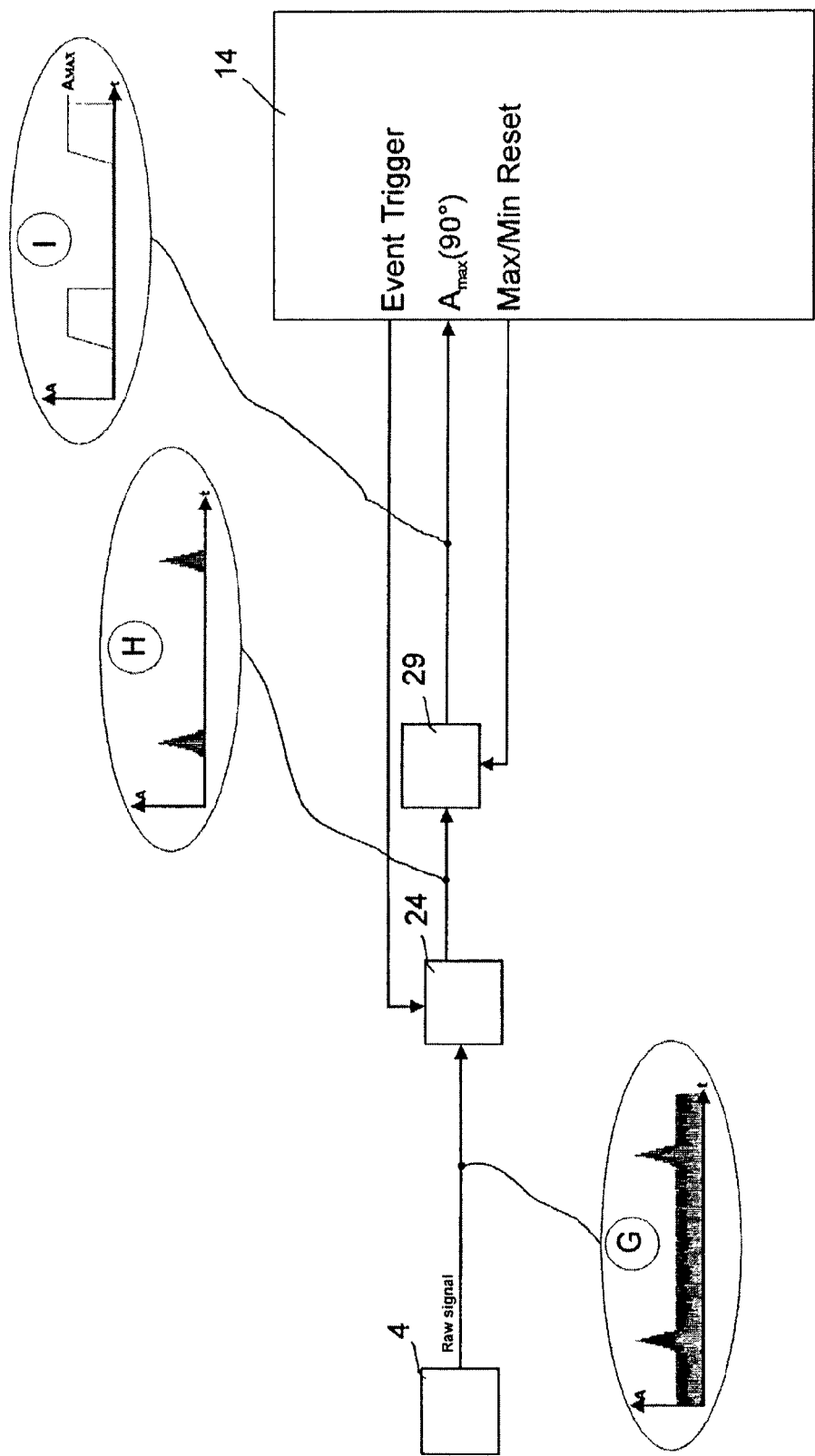
FIG. 5 is a schematic view illustrating the second reception signal conditioning.

According to FIG. 5, the maximum value of the precipitation-related reception signal at 90° is determined from the provided raw signal G by means of the signal separating unit 24 and the maximum value detector corresponding to the process described for the signal conditioning at 32° for every precipitation particle detected at 32° (signal sequences H and I).

Figure 6:
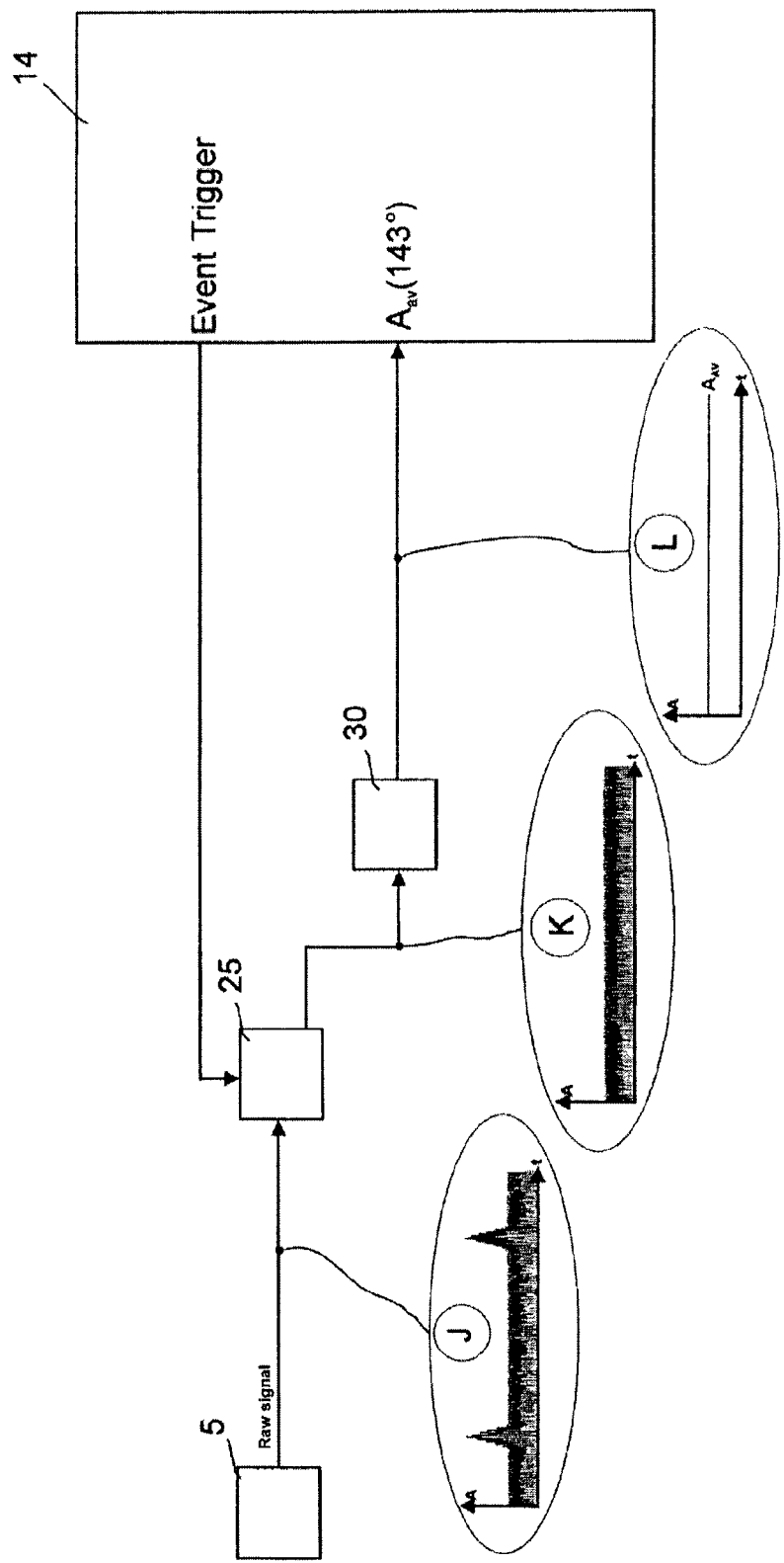
FIG. 6 is a schematic view illustrating the third reception signal conditioning.

According to FIG. 6, the raw signal J obtained by the receiver 5 at 143° is freed from signal components not caused by precipitation by means of the signal separating unit 25 and is conveyed after averaging through the lowpass 30 to the processing unit 14 (signal sequences K and L).

When a precipitation particle penetrates the measurement volume 16, a signal break-in in the direct light measurement can be determined by means of the receiver 2. According to FIG. 7, signal sequence M is generated. In order to evaluate this process using measurement technology, the minimum direct light measurement value (signal sequence P) is determined for every particle detected at 32° by means of the signal separating unit 26 and the minimum value detector 31 and is fed to the processing unit 14. The minimum value detector 31 is reset after the particle has exited from the measurement volume 16. Further, the reception signal (signal sequence N) that was obtained at 0° and freed from precipitation-related signal components by the signal separating unit 26 is fed to the lowpass 32, so that the precipitation-related mean value (signal sequence O) is subsequently made available to the processing unit 14.

The following relationships and evaluation mechanisms are to be used as a basis for the following further processing and evaluation of the obtained signals. The information relates to the use of a light wavelength in the visible spectral range. The angular ranges mentioned above are shifted for other light wavelengths. In general, however, the relationships and procedures noted in the following also apply in the latter case.

Figure 8:
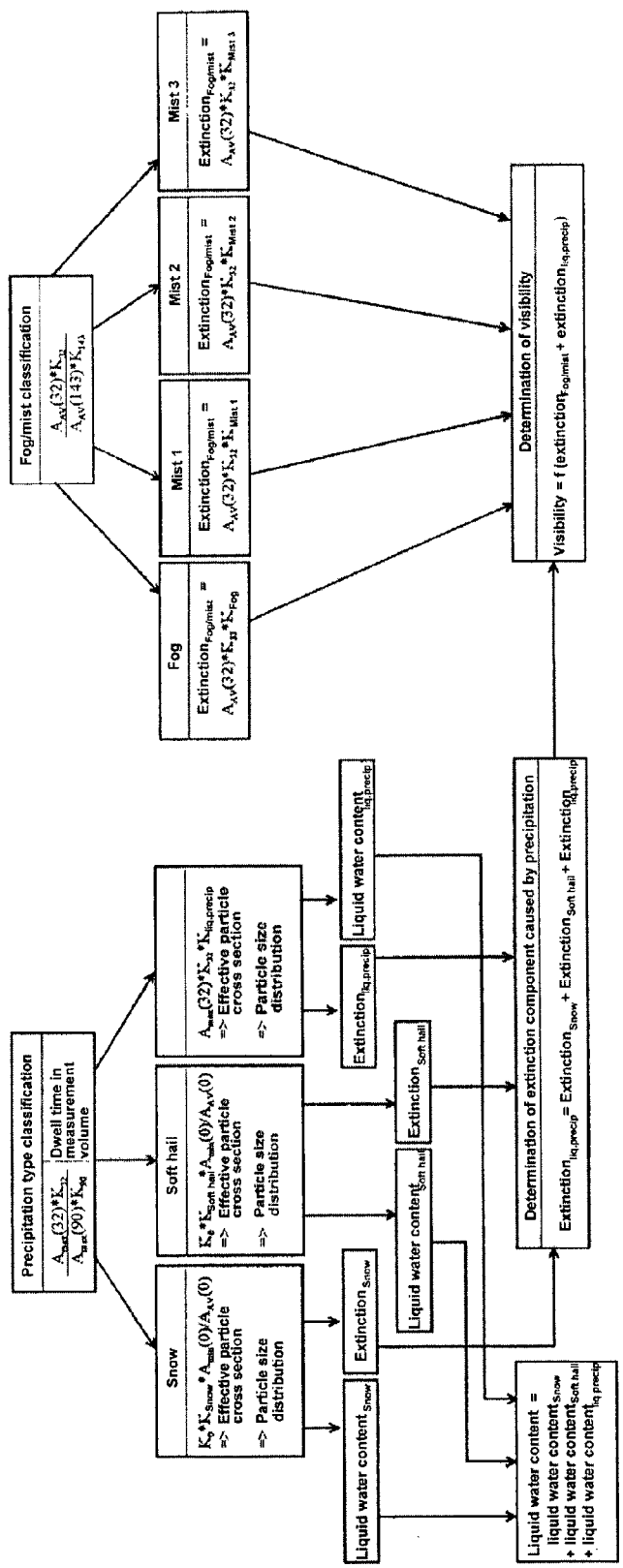
FIG. 8 shows the principle of the reception signal evaluation.

FIG. 8 is a schematic view illustrating the reception signal evaluation:

1. An optimal evaluation of fog phenomena can only be carried out at a scattering angle of about 20° to 40°. In this optimal angular range for fog, an equality evaluation of mist results in an uncertainty of up to 60% for visibility determination. By parallel evaluation of the measurements (quotient formation) at 32° and 143°, conclusions can be arrived at regarding the prevailing mist phenomenon. This enables a phenomenon-dependent evaluation of the reception signal at 20° to 40°. The measurement uncertainty can accordingly be kept to values of less than 10% for all known fog and mist phenomena.

After averaging the conditioned scattering signals at 32° ($A_{AV}(32)$) and 143° ($A_{AV}(143)$), a typical device constant $K_{32}$ and $K_{143}$ is applied (unit 1/Vm). Subsequently, the two measurements are placed in a ratio (quotient formation) in order to conclude whether there is fog or one of several mist phenomenon groups (mist 1, mist 2 and mist 3). After the phenomenon category has been determined, the extinction component not related to precipitation can be calculated from the scattering signal obtained at 32° by taking into account a correspondingly adapted evaluation factor ($K_{fog}$, $K_{mist1}$, $K_{mist2}$ or $K_{mist3}$) and the typical device constant $K_{32}$.

In this connection, it is not mandatory that the mist phenomena be classified into mist groups. A dynamic reception signal adaptation depending on the quotient of $K_{32}*A_{AV}(32)$ and $K_{143}*A_{AV}(143)$ can also be applied for optimized mist evaluation.

2. Evaluation of the signal components caused by precipitation:

As has already been shown, the process described above for individual particle detection enables time-discrete handling of precipitation particles which penetrate the scattered light measurement volume. Accordingly, the scattering signal amplitude and the dwell time in the measurement volume are available for each of these particles. The scattered light signal at a lateral scattering angle involves a particularly high information content about the presence of liquid precipitation, solid precipitation, or rain, snow or soft hail. When a precipitation particle is detected when measuring at 32°, the type of precipitation is decided upon simultaneously by means of the quotient of the measurement values obtained at 32° ($A_{max}(32)$) and 90° ($A_{max}(90)$) (after applying the typical device constants $K_{32}$ and $K_{90}$) and by means of the dwell time in the measurement volume.

At the 32-degree measurement angle, liquid precipitation events can be evaluated in a representative manner by introducing the device constant $K_{32}$ and taking into account the adaptation factor $K_{liq\ precip}$ for liquid precipitation. This procedure makes it possible to determine the following parameters:

extinction through liquid precipitation;

particle size distribution for liquid precipitation and, therefore, distinguishing between drizzle and rain;

intensity of the liquid precipitation.

The integral of the amplitude over the dwell time of the particle event is proportional to the effective cross-sectional area of the particle and, therefore, to the particle extinction. When the individual particle extinctions are summed over a given time period, this provides the extinction component for liquid precipitation. Further, the liquid water content can be determined for every liquid precipitation particle being considered and can also be summed for a given time period. This leads to precipitation intensity information for liquid precipitation. If there is solid precipitation, no reliable conclusions can be derived from the scattered light information regarding the corresponding extinction component or precipitation intensity. However, the extinction component caused by solid precipitation and the corresponding precipitation intensity can be determined when the effective cross-sectional area of the particle is known.

A measurement at 0° enables direct determination of this effective cross-sectional area of the particle by evaluating the relative transmission break-in that occurs when a particle penetrates the measurement volume. The relative transmission break-in can be calculated by the quotient of the measured values $A_{min}(0)$ and $A_{AV}(0)$ and by taking into account another device constant for the direct receiver $K_0$. In addition, a corresponding adaptation factor must be applied ($K_{snow}$ or $K_{soft\ hail}$) depending on whether there is snow or soft hail.

This measurement is only carried out when a precipitation particle has been detected at 32° and identified as solid precipitation by the additional measurement at 90°. The integral of the amplitude over the dwell time of the detected relative signal break-in of the direct light measurement is proportional to the effective cross-sectional area of the particle and, therefore, to the particle extinction. When the individual particle extinctions are summed over a time period under consideration, the extinction component for solid precipitation is given. Further, the liquid water content can be determined for every solid precipitation particle being considered and can also be summed for a given time period. This gives the precipitation intensity information for solid precipitation.

The total precipitation-related extinction component can be determined by adding the partial extinctions for snow, soft hail and liquid precipitation.

3. Evaluation of the signal components caused by precipitation and the signal components not caused by precipitation For final determination of visibility, the signal components not caused by precipitation and the signal components caused by precipitation are added together and converted to visibility by taking into account the contrast threshold.

While the foregoing description and drawings represent the present invention, it will be obvious to those skilled in the art that various changes may be made therein without departing from the true spirit and scope of the present invention.

REFERENCE NUMBERS 1 light transmitter
2 receiver
3 receiver
4 receiver
5 receiver
6 postamplifier
7 postamplifier
8 postamplifier
9 postamplifier
10 synchronous rectifier
11 synchronous rectifier
12 synchronous rectifier
13 synchronous rectifier
14 processing unit
15 modulation generator
16 measurement volume
17 reception signal conditioning
18 reception signal conditioning
19 reception signal conditioning
20 reception signal conditioning
21 lowpass
22 threshold switch
23 signal separating unit
24 signal separating unit
25 signal separating unit
26 signal separating unit
27 lowpass
28 maximum value detector
29 maximum value detector
30 lowpass
31 minimum value detector
32 lowpass
33 evaluating electronics
34 reception signal conditioning unit

What is claimed is:

1. A method for determining visibility, amount of precipitation and type of precipitation comprising the steps of:

illuminating a defined spatial area by using an intensity modulated light transmitter of selected wavelength and adapted intensity;

receiving light which is scattered by aerosol conglomeration and, in the case of precipitation, additionally by single precipitation particles of liquid or non-liquid types from an angle range of 20° to 40° to a radiation axis of the light transmitter by a light receiver in a suitable visual field, in a narrow band and with adapted sensitivity for creating a first reception signal, whereas spatial overlap of a viewing field of the light receiver and a light transmitter beam defines a measurement volume MV;

receiving light which is scattered by aerosol conglomeration and, in the case of precipitation, additionally by single precipitation particles of the liquid or non-liquid types from an angle range of 70° to 120° to the radiation axis of the light transmitter by a light receiver in the suitable visual field in a narrow band and with adapted sensitivity for creating a second reception signal, whereas spatial overlap of the light receiver viewing field and the light transmitter beam defines a measurement volume which is similar to the measurement volume MV;

detecting precipitation particles which are passing the measurement volume MV by evaluating the first reception signal which derived from light which is obtained at 20° to 40° to the radiation axis of the light transmitter, said first reception signal having a mean value and a spontaneous value, in such a way that the mean value of said first reception signal is compared to the spontaneous value of the first reception signal, and a corresponding particle detection signal is given to a processing unit, as long as the spontaneous value of the reception signal exceeds the mean value of the first reception signal;

determining a dwell time of each detected precipitation particle in the measurement volume MV by the processing unit utilizing the duration of the particle detection signal;

determining a maximum signal value Amax(32) of the spontaneous first reception signal derived from the light which is obtained at 20° to 40° to the radiation axis of the light transmitter during the dwell time of each detected precipitation particle in the measurement volume MV by the processing unit;

determining a signal average Aav(32) of the first reception signal derived from the light which is obtained at 20° to 40° to the radiation axis of the light transmitter, whereas influence of each detected precipitation particle on this signal average Aav(32) is masked out by interrupting an averaging process for the dwell time of each detected precipitation particle, utilizing the duration of the particle detection signal;

determining a maximum signal value Amax(90) of the spontaneous second reception signal derived from the light which is obtained at 70° to 120° to the radiation axis of the light transmitter during the dwell time of each detected precipitation particle in the measurement volume MV by the processing unit, utilizing the duration of the particle detection signal;

determining an extinction component which is not caused by precipitation based on the signal average Aav(32) within the framework of the processing unit; and determining whether a detected precipitation particle is of liquid or non-liquid type based on comparison of Amax(32), the maximum signal value of the spontaneous first reception signal derived from the light obtained at 20° to 40° to the radiation axis of the light transmitter during the dwell time of each detected precipitation particle, and Amax(90), the maximum signal value of the spontaneous second reception signal derived from the light obtained at 70° to 120° to the radiation axis of the light transmitter during the dwell time of each detected precipitation particle, based on knowledge of a typical angle-dependent scattering behavior of precipitation particles of liquid and non-liquid type within the framework of the processing unit.

2. The method according to claim 1, wherein the size of each detected liquid type precipitation particle is evaluated within the framework of the processing unit based on determined dwell time of each detected precipitation particle, maximum signal value of the spontaneous first reception signal Amax(32) derived from the light obtained at 20° to 40° to the radiation axis of the light transmitter during the dwell time of each detected precipitation particle and the signal average Aav(32) of the first reception signal derived from the light which is obtained at 20° to 40° to the radiation axis of the light transmitter.

3. The method according to claim 2, wherein the particle size of each detected liquid type precipitation particle is stored within the framework of the processing unit for a defined observation period.

4. The method according to claim 3, wherein liquid precipitation particle size distribution, liquid water content for liquid precipitation and liquid precipitation based extinction component are evaluated within the framework of the processing unit based on stored particle sizes of detected liquid type precipitation particles within the observation period.

5. The method according to claim 4, wherein the light which is emitted by the light transmitter is received by a light receiver at an angle of 0° to the radiation axis of the light transmitter in a suitable visual field, in a narrow band and with adapted sensitivity for creating a third reception signal, whereas spatial overlap of the light receiver viewing field and the light transmitter beam defines a measurement volume which incorporates the measurement volume MV, in order to determine a signal average Aav(0) of the third reception signal derived from the light which is obtained at 0° to the radiation axis of the light transmitter, whereas influence of each detected non-liquid type precipitation particle on this signal average Aav(0) is masked out by interrupting the averaging process for the dwell time of each detected and as non-liquid type determined precipitation particle, utilizing the duration of the particle detection signal for particles detected at an angle of 20° to 40°, and to determine a minimum signal value Amin(0) of the spontaneous third reception signal derived from the light which is obtained at 0° to the radiation axis of the light transmitter during the dwell time of each detected and as non-liquid type determined precipitation particle by the processing unit, utilizing the duration of the particle detection signal for particles detected at an angle of 20° to 40°.

6. The method according to claim 5, wherein the particle size of each detected and as non-liquid type determined precipitation particle is evaluated within the framework of the processing unit based on the dwell time of each detected precipitation particle, utilizing the duration of the particle detection signal for particles detected at an angle of 20° to 40°, an associated minimum signal value Amin(0) of the spontaneous reception signal derived from the light which is obtained at 0° to the radiation axis of the light transmitter during the dwell time of each detected precipitation particle, and the signal average Aav(0) of the reception signal derived from the light which is obtained at 0° to the radiation axis of the light transmitter, whereas the influence of each detected non-liquid type particle on said signal average Aav(0) is masked out by interrupting the averaging process for the dwell time of each detected and as non-liquid type determined precipitation particle.

7. The method according to claim 6, wherein the particle size of each detected non-liquid type precipitation particle is stored within the framework of the processing unit for a defined observation period.

8. The method according to claim 7, wherein non-liquid precipitation particle size distribution, the non-liquid precipitation liquid water content and non-liquid precipitation based extinction component are evaluated within the framework of the processing unit based on the stored particle sizes of the detected non-liquid type precipitation particles which are detected within the observation period.

9. The method according to claim 8, wherein a definitive determination of prevailing precipitation phenomenon is also carried out in the case of mixed liquid and non-liquid type precipitation based upon detected liquid and non-liquid precipitation particle sizes and distributions stored within the framework of the processing unit for a defined observation period.

10. The method according to claim 4, wherein addition of the extinction component which is not caused by precipitation and the liquid precipitation based extinction component which are determined within the observation period leads to determination of extinction in its entirety, without taking into account the non-liquid precipitation based extinction component, and which is subsequently converted into a visibility while taking into account a contrast threshold.

11. The method according to claim 8, wherein addition of liquid water contents determined for liquid, and non-liquid and type precipitation in the observation period, is utilized for determining the entire accumulated liquid water amount of precipitation and the liquid water amount per time unit (precipitation intensity).

12. The method according to claim 8, wherein addition of liquid precipitation based extinction component and non-liquid precipitation based extinction component leads to the determination of the totality of extinction caused by precipitation.

13. The method according to claim 12, wherein addition of totality of extinction caused by precipitation and of the extinction component not caused by precipitation leads to determination of extinction in its entirety, and which is subsequently converted into a visibility while taking into account a contrast threshold.

14. The method according to claim 1, additionally comprising the steps of:
receiving light which is scattered by aerosol conglomeration and, in the case of precipitation, additionally by single precipitation particles of liquid or non-liquid types from an angle range of 140° to 150° to the radiation axis of the light transmitter by a light receiver in a suitable visual field in a narrow band and with adapted sensitivity for creating a fourth reception signal, whereas spatial overlap of the light receiver viewing field and light transmitter beam defines a measurement volume which is similar to the measurement volume MV;
determining a signal average Aav(143) of the fourth reception signal derived from the light which is obtained at 140° to 150° to the radiation axis of the light transmitter, whereas influence of each detected precipitation particle on said signal average Aav(143) is masked out by interrupting an averaging process for the dwell time of each detected precipitation particle, utilizing the duration of the particle detection signal;
determining prevailing fog phenomenon or mist phenomenon based on knowledge of corresponding typical angle-dependent scattering behavior by comparing signal averages Aav(32) and Aav(143) within the framework of the processing unit.

15. The method according to claim 14, wherein a valuation which is correspondingly adapted to determined prevailing fog phenomenon or mist phenomenon is carried out and extinction component not caused by precipitation is subsequently determined for signal average Aav(32).

16. The method according to claim 15, wherein addition of the extinction component not caused by precipitation and which is adapted to the determined prevailing fog phenomenon or mist phenomenon and totality of extinction caused by precipitation leads to determination of the extinction in its entirety, and which is subsequently converted into a visibility while taking into account a contrast threshold.

17. A method for determining visibility comprising the steps of:
illuminating a defined spatial area by using an intensity modulated light transmitter of selected wavelength and adapted intensity;
receiving light which is scattered by aerosol conglomeration and, in the case of precipitation, additionally by single precipitation particles of liquid or non-liquid types from an angle range of 20° to 40° to a radiation axis of the light transmitter by a light receiver in a suitable visual field, in a narrow band and with adapted sensitivity for creating a first reception signal, whereas spatial overlap of a viewing field of the light receiver and a light transmitter beam defines the measurement volume MV;
receiving light which is scattered by aerosol conglomeration and in the case of precipitation additionally by single precipitation particles of liquid or non-liquid types from an angle range of 140° to 150° to the radiation axis of the light transmitter by a light receiver in the suitable visual field in the narrow band and with adapted sensitivity for creating a fourth reception signal, whereas spatial overlap of the light receiver viewing field and the light transmitter beam defines a measurement volume which is similar to the measurement volume MV;
detecting precipitation particles which are passing the measurement volume MV by evaluating a reception signal which derive from light which is obtained at 20° to 40° to the radiation axis of the light transmitter, said first reception signal having a mean value and a spontaneous value, in such a way that the mean value of the first reception signal is compared to the spontaneous value of the first reception signal, and a corresponding particle detection signal is given to a processing unit, as long as the spontaneous value of the reception signal exceeds the mean value of the reception signal;
determining a signal average Aav(32) of the first reception signal derived from the light which is obtained at 20° to 40° to the radiation axis of the light transmitter, whereas influence of each detected precipitation particle on said signal average Aav(32) is masked out by interrupting an averaging process for a dwell time of each detected precipitation particle, utilizing the duration of the particle detection signal;
determining a signal average Aav(143) of the fourth reception signal derived from the light which is obtained at 140° to 150° to the radiation axis of the light transmitter, whereas the influence of each detected precipitation particle on this signal average Aav(143) is masked out by interrupting the averaging process for the dwell time of each detected precipitation particle, utilizing the duration of the particle detection signal; and
determining prevailing fog phenomenon or mist phenomenon based on knowledge of corresponding typical angle-dependent scattering behavior by comparing the signal averages Aav(32) and Aav(143) within a the framework of the processing unit.

18. The method according to claim 17, wherein a valuation which is correspondingly adapted to a determined prevailing fog phenomenon or mist phenomenon is carried out and an extinction component not caused by precipitation is subsequently determined for the signal average Aav(32).

19. The method according to claim 18, wherein the determined extinction component not caused by precipitation is converted into a visibility while taking into account a contrast threshold without taking into account an extinction component caused by precipitation.

* * * * *